United States Patent
Burke

[11] Patent Number: 5,899,900
[45] Date of Patent: May 4, 1999

[54] HIGH FREQUENCY TWEEZER TYPE EPILATOR

[76] Inventor: Robert E. Burke, Belleair Beach, Fla.

[21] Appl. No.: 08/963,134

[22] Filed: Nov. 3, 1997

[51] Int. Cl.$^6$ .................................................. A61B 17/41
[52] U.S. Cl. ............................................... 606/43; 606/36
[58] Field of Search ................................. 606/36, 43, 44, 606/51, 52, 133

[56] References Cited

U.S. PATENT DOCUMENTS

| | | | |
|---|---|---|---|
| 4,174,713 | 11/1979 | Mehl | 606/43 |
| 5,049,148 | 9/1991 | Mehl | 606/43 |
| 5,169,398 | 12/1992 | Glaros | 606/36 |

*Primary Examiner*—Michael Peffley
*Attorney, Agent, or Firm*—Ronald E. Smith, P.A.

[57] ABSTRACT

An epilator includes a pair of tweezers mounted at the leading end of a hollow wand body. An electrical circuit board for generating a radio frequency current is mounted in the trailing end of the wand body. The trailing end of the wand body is coated with a metabolized conductive coating to shield against electromagnetic interference. The tweezers are maintained in normally spaced apart relation to one another by a bias member that is compressed by a manually-operated actuator. The bias member includes an extension member that is in continuous contact with a first tweezer member and which makes contact with an electrical contact member mounted in the second tweezer member when the tweezer members are brought into hair-gripping relation to one another by actuator-driven compression of the bias member. The contact closes an electrical circuit through the circuit board so that the gripped hair is subjected to a radio frequency that deadens adjacent nerve cells and causes roots of the gripped hair to release their grip so that the hair is painlessly extracted. The wand includes a socket for releasable connection with a plug that is in electrical communication with a remote power source.

11 Claims, 4 Drawing Sheets

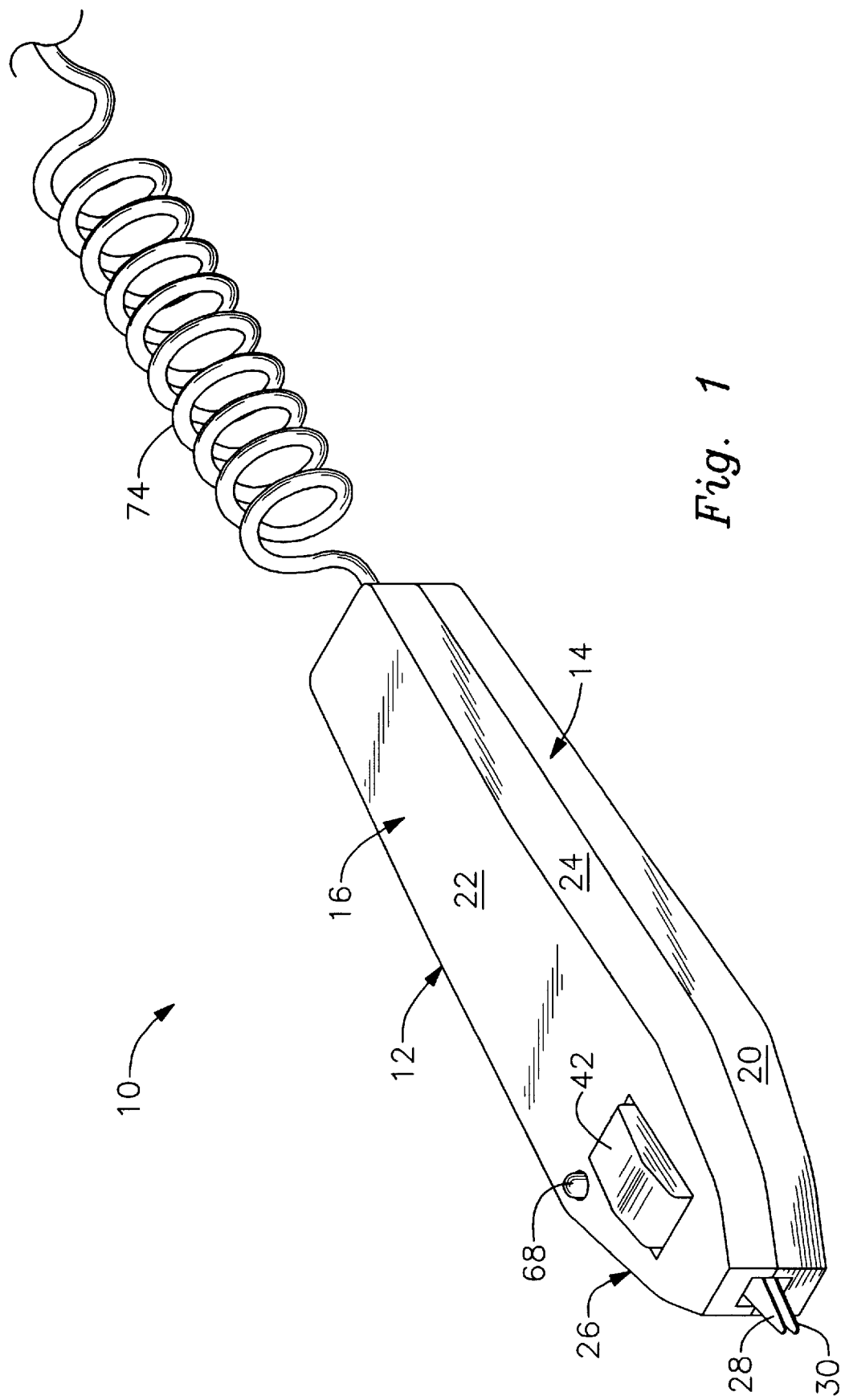

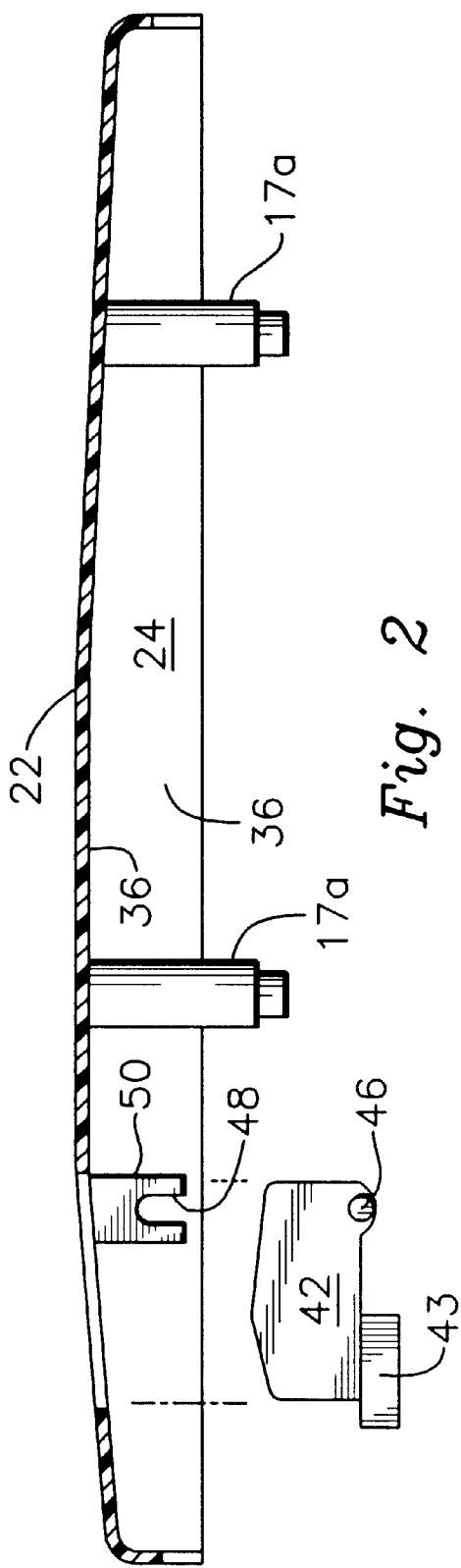
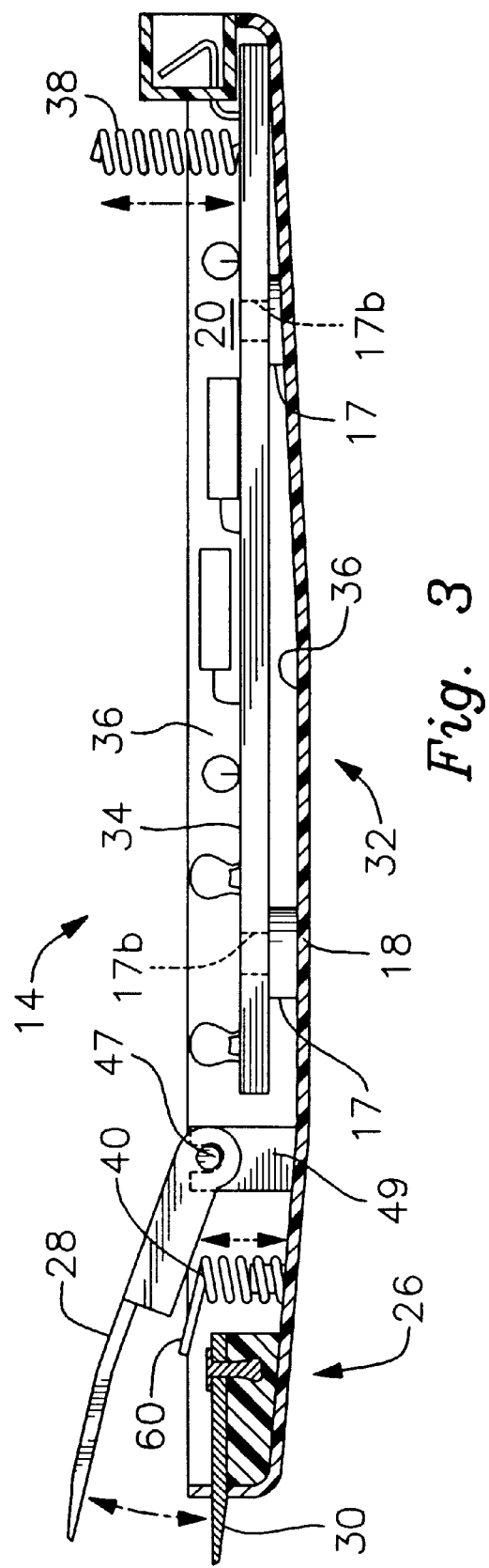

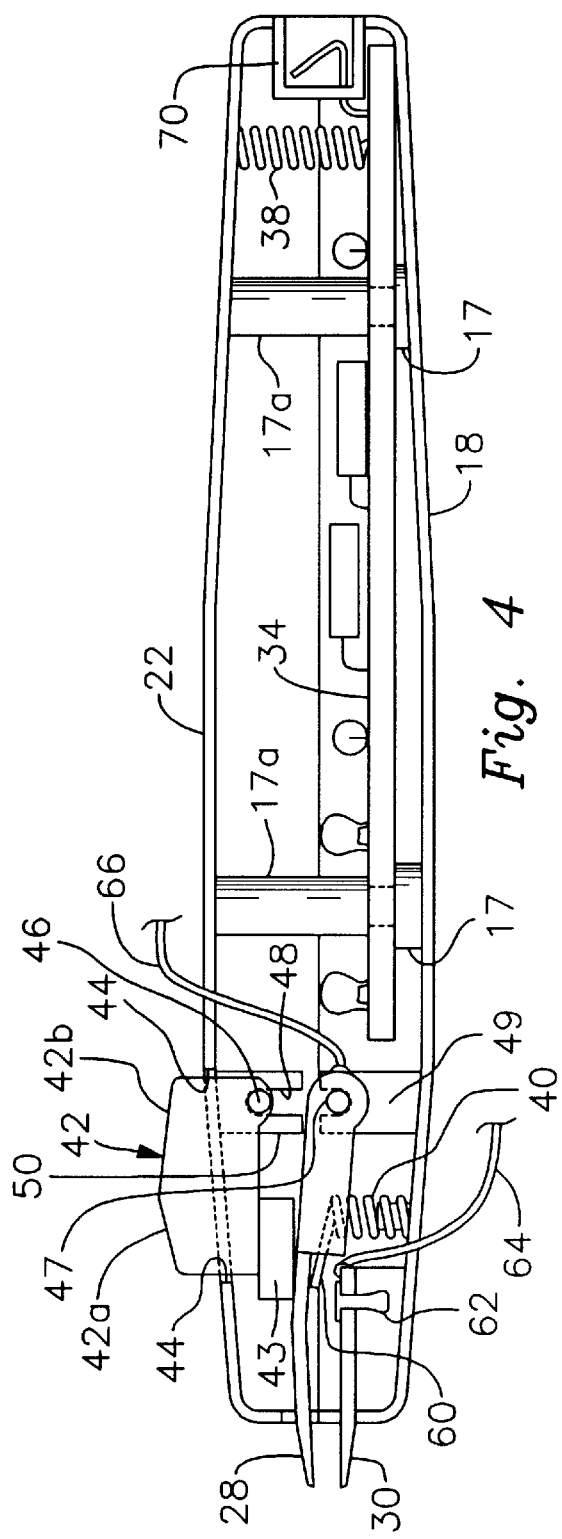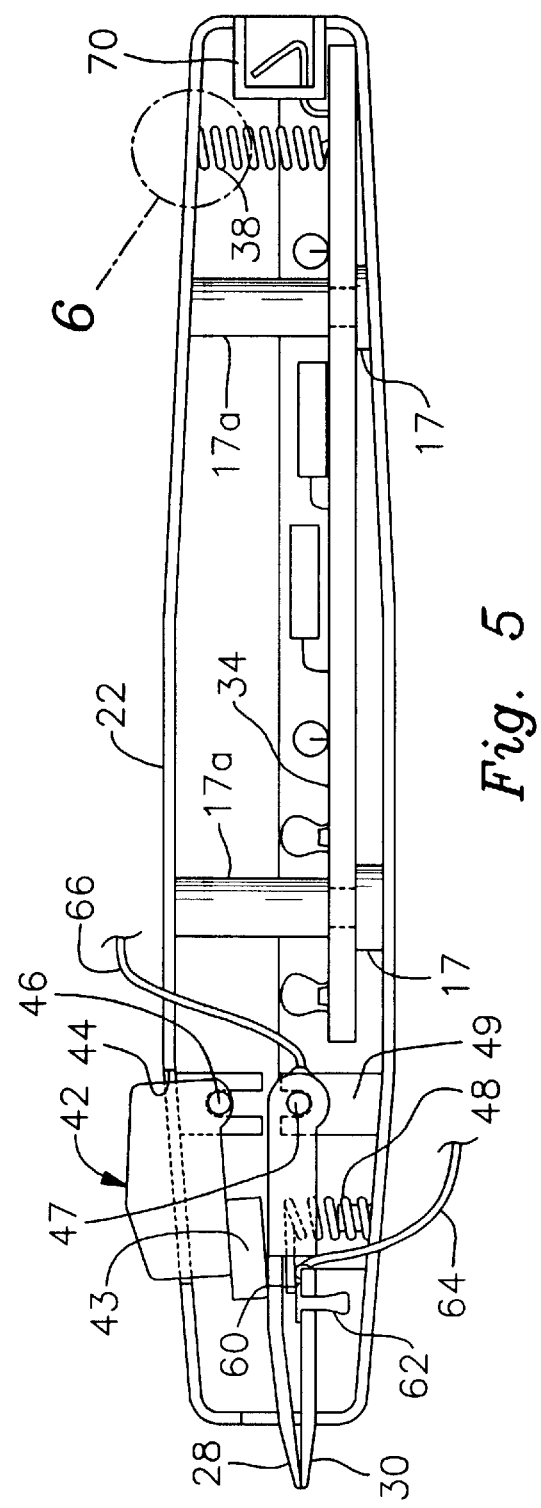

HIGH FREQUENCY TWEEZER TYPE EPILATOR

BACKGROUND OF THE INVENTION

1. Field of the Invention

This invention relates, generally, to devices that remove hair. More particularly, it relates to an epilator device that employs radio frequency radiation for permanent hair removal in the absence of pain.

2. Description of the Prior Art

Radio frequency (RF) hair removers, known as epilators, are well-known. Typically, they include a hand-held wand, a tweezer means including a pair of normally spaced apart tweezer members positioned at the leading end of the wand, a mechanical means controlled by an operator for causing the tweezer members to selectively converge and separate from one another, a remote RF generator, an operator-controlled on-off switch for activating the remote RF generator, and shielded power cord means for electrically connecting the remote RF generator and the tweezer members to comply with applicable federal standards relating to the emission of electromagnetic and RF interference.

There are a number of drawbacks with the known epilators. First of all, the remote RF generator and the power cord that interconnects it to the tweezer members must be shielded. Moreover, the mechanical means for causing the tweezer members to converge into hair-grasping relation to one another is somewhat complex and adds further manufacturing expense. Further, the on-off switch for activating the remote RF generator is a separate unit from said mechanical means for causing the tweezers to converge and that adds still another expense to the fabrication of the wand.

The known tweezer members are also prone to oxidation and thus have a truncated useful lifetime.

Still another shortcoming of known epilators is that they include tweezer members having sharp hair-gripping ends. As a result, a grasped hair may be cut off by the tweezers above the skin line so that it simply grows back. The sharp ends also provide a poor gripping means so that a strand of hair may simply slip out of the grasp of the tweezer members when the operator tries to pull the strand out.

The known epilators also include a power source, such as a battery, disposed within the wand. This prevents electrical connection of the wand to alternative remote power sources such as an automotive or motor home cigarette lighter plug, a remote battery pack, and the like.

However, in view of the art considered as a whole at the time the present invention was made, it was not obvious to those of ordinary skill in this art how the observed drawbacks could be overcome.

SUMMARY OF THE INVENTION

The longstanding but heretofore unfulfilled need for an apparatus that overcomes the limitations of the prior art is now met by a new, useful, and nonobvious invention. The present invention includes an epilator including a hollow wand body having an inner surface and an outer surface. The wand body has a leading end and a trailing end, and an electrical circuit board for generating a predetermined radio frequency is mounted within the trailing end of the wand body.

A metabolized conductive coating is formed on the inner surface of the trailing end of the wand body to inhibit emission of electromagnetic radiation generated by the components mounted on the electrical circuit board; the inner surface of the leading end is free of said metabolized conductive coating.

A pair of opposed first and second tweezer members are mounted at the leading end of the wand body. A bias means is positioned between the first and second tweezer members to maintain them in a normally open configuration when the bias means is in repose. An actuator member for compressing the bias means is provided so that that the first and second tweezer members are brought into contacting relation to one another when the actuator member is manipulated. An electrically conductive extension member that extends in a leading direction from the bias means and which is in contact with a first preselected tweezer member when the bias means is in repose makes electrical contact with a second preselected tweezer member when the tweezer members are brought into hair-gripping relation to one another. The contact by the extension member closes an electrical circuit that includes the components of the electrical circuit board when the first and second tweezer members are brought into said hair-gripping relation to one another so that a strand of hair gripped by the first and second tweezer members is subjected to an efficacious radio frequency, said radio frequency numbing nerve endings in the vicinity of said hair so that the hair may be painlessly uprooted.

A general object of this invention is to overcome all of the limitations of the epilators of the prior art.

A more specific object is to provide a hand-held epilator having RF generating circuitry packaged within the epilator wand.

An object closely related to the foregoing object is to provide an epilator wand having RF generating circuitry packaged therewithin that is shielded against RF and electromagnetic interference.

Another important object is to provide an epilator having a remote power source and an adaptor means for electrically connecting the epilator wand to said remote power source.

An object related to the provision of a shielded wand and the provision of a remote power source is to enable provision of an unshielded electrical conductor for interconnecting said remote power source to said circuitry in said wand.

Another important object is to provide an epilator having a mechanical structure that combines the functions of an on-off switch and the functions of a mechanical means for selectively converging and separating the normally open tweezer members of an epilator so that the operator need not deal with a separate on-off switch.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a perspective view of an exemplary embodiment of the invention when in its assembled configuration;

FIG. 2 is a partially sectional side elevational view of the upper housing of the exemplary embodiment;

FIG. 3 is a partially sectional side elevational view of the lower housing of said embodiment;

FIG. 4 is a partially sectional side elevational view of the lower and upper housings when connected to one another, depicting the tweezer members when spaced apart from one another;

FIG. 5 is a partially sectional side elvational view of said upper and lower housings when connected to one another, depicting the tweezer members when in contact with one another;

DETAILED DESCRIPTION OF THE PREFERRED EMBODIMENT

Figure 6:
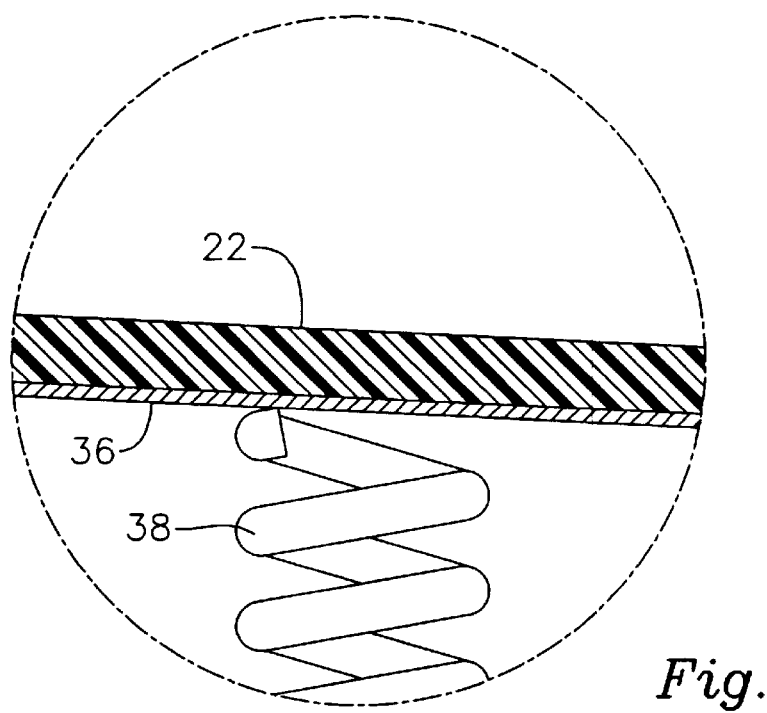
FIG. 6 is a detailed view of the encircled area denoted 7 in FIG. 5.

Referring now to FIGS. 1–3, it will there be seen that an exemplary embodiment of the invention is denoted as a whole by the reference numeral 10.

Epilator 10 includes a hollow wand body 12 having a lower shell 14 and an upper shell 16. Lower shell 14 includes a bottom wall 18 and upstanding side walls 20 mounted about the periphery thereof. Upper shell 16 includes a top wall 22 and side walls 24 mounted about the periphery thereof in depending relation thereto. Side walls 20 and 24 interlock with one another in conventional fashion to collectively define said hollow wand body 12.

The leading end of hollow wand body 12 is denoted 26 as a whole and houses a pair of normally spaced apart tweezer members 28 and 30.

The trailing end of hollow wand body 12 is denoted 32 and houses an electronic circuit board 34; said circuit board contains conventional circuitry for generating radio frequency (RF) radiation at a frequency known to have hair removal efficacy. It is secured to nonconductive post members, collectively denoted 17, that project upwardly from bottom wall 18 of lower shell 14.

Significantly, the respective inner surfaces of bottom wall 18, its upstanding side walls 20, upper wall 22 and its depending side walls 24 that lie within trailing end 32 of wand body 12 are coated with a shielding means that inhibits emission of radio frequency and electromagnetic interference; the outer surfaces of wand body 12 are not coated.

The shielding preferably takes the form of a metallic, metabolized conductive coating 36, best depicted in FIG. 6, that is applied by any suitable means such as plasma spraying or the like. Leading end 26 of hollow wand body 12 is not shielded because tweezer members 28 and 30 must be insulated from said metabolized coating 36.

As perhaps best understood in connection with FIGS. 4 and 5, an electrical conductor, preferably in the form of a coil spring 38, extends between circuit board 34 and said coated top wall 22 of upper shell 16, respectively, to complete an electromagnetic interference-shielding circuit therebetween when wand body 12 is in its assembled configuration. Specifically, a first end of spring 38 must be soldered to said circuit board 34 and a second end thereof must abut coating 36. As depicted, said coil spring is preferably positioned at the trailing end of wand body 12.

In a preferred embodiment, upper tweezer 28 is movably mounted and lower tweezer 30 is not. A bias means such as coil spring 40 (FIGS. 4 and 5) extends between bottom wall 18 and upper tweezer member 28 and maintains said upper tweezer member in its normal configuration, i.e., in spaced relation to lower tweezer member 30. Bias means 40, like tweezer members 28 and 30, is insulated from coating 36. Thus, compression of bias means 40 brings upper tweezer 28 into contacting relation to lower tweezer 30 when no hair is positioned therebetween. Said compression is accomplished by manually pushing down on pivotally mounted actuator 42 which serves the dual purpose of compressing said bias means as aforesaid and of initiating or activating current flow through the electrical components mounted on circuit board 34, i.e., actuator 42 combines a mechanical hair-gripping function and an on-off switch function.

More particularly, actuator 42, which has a forwardly sloped part 42a and a rearwardly sloped part 42b for ergonomic purposes, is mounted so that it extends through an opening 44 formed in top wall 22 of upper shell 16 which opening accommodates and guides said actuator and enables its facile manipulation by the epilator operator. A pair of transversely extending pins 46, only one of which is visible when device 10 is viewed in side elevation, are integrally formed on the lowermost, trailing end of actuator 42 and are pivotally received in downwardly opening recesses, only one of which is visible as at 48, said recesses being formed in mounting members 50 which depend from top wall 22. Note member 43 which is integrally formed with actuator 42 at its leading, lowermost end; member 43 is the part of actuator 42 that actually makes physical contact with upper tweezer member 28.

Upper tweezer member is also pivotally mounted in a similar manner; specifically, a pair of transversely disposed pins 47, only one of which is visible, are pivotally disposed within upwardly opening recesses, not numbered to avoid cluttering the drawings, formed in the uppermost ends of mounting members 49 which project upwardly from bottom wall 18 of lower housing 14. Note that the bias of spring 40 urges the leading end of upper tweezer member 28 in an upward direction and the trailing end of said tweezer member 28 in a downwardly direction so that pins 47 are maintained in said unnumbered recesses, said spring 40 being positioned between said leading end and said recesses.

A conductive extension means 60 is integrally formed with and extends in a leading direction from bias means 40 and bears against the underside of upper tweezer member 28 when actuator 42 is in repose. When epilator 10 is in use, the operator positions a strand of hair between tweezer members 28 and 30, and presses down on actuator 42 against the bias of bias means 40. Extension means 50, which may take the form of a displaced uppermost coil of a coil spring as depicted, makes contact with an electrical contact 62 that is mounted to bottom tweezer 30, and which projects slightly upwardly therefrom, when a strand of hair is compressed between said upper and lower tweezer members; such contact completes an electrical circuit through the unnumbered components on circuit board 34 so that electromagnetic energy at the efficacious radio frequency is applied to said tweezer members and hence to said hair and its roots at said moment. The circuit is completed because elongate flexible conductor 64 extends from contact 62 as depicted in FIGS. 4 and 5 to the circuit board and elongate flexible conductor 66 extends from said upper tweezer 28 to said circuit board.

A light-emitting diode 68 (FIG. 1) which extends through an opening formed in top wall 16 of housing 12, is also activated by the closing of said circuit, its light indicating to the operator that the circuit has been completed.

Thus, the operator need not throw an on-off switch as a separate procedure apart from the procedure for bringing the opposing tweezer members together, as required in earlier epilators, because the means for bringing the opposing tweezer members together includes said extension means 50 and said contact 62 which serve as the contacts of a single pole, single throw on-off switch.

Note that circuit board 34 must not come into contact with metabolized conductive coating 36; accordingly, it is supported by nonconductive pegs or posts, collectively denoted 17 as aforesaid. Nonconductive posts 17a, 17a, which depend from top wall 22 of upper housing 16, extend through openings 17b (FIG. 3) formed in circuit board 34 and join with said posts 17 to further interlock the upper and lower halves of housing 12 together and to hold circuit board 34 in place.

The respective hair-pinching distal ends of tweezer members 28, 30 are blunted and have cross-hatching or knurling formed therein to prevent cutting of hair and to enhance the hair-gripping qualities of said distal ends. Moreover, tweezer members 28, 30 are gold-plated to inhibit oxidation; the preferred thickness of the plating is about ten microns.

Figure 7:
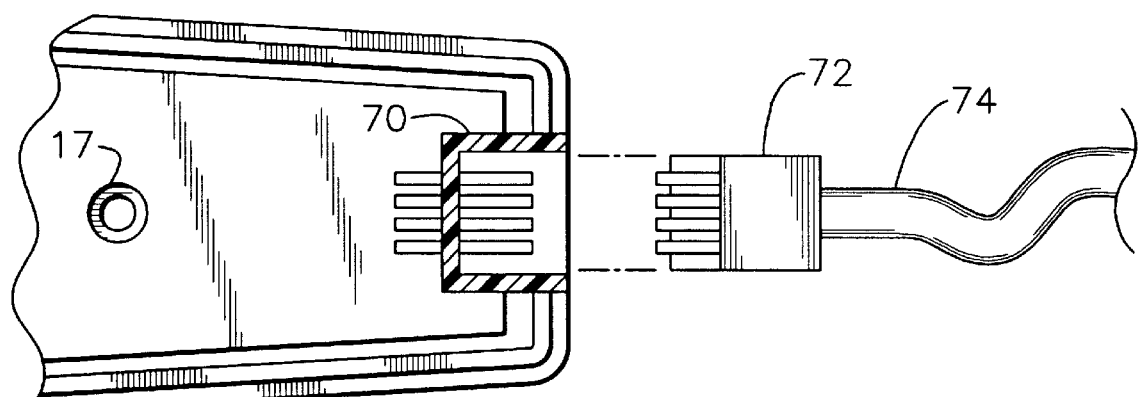
FIG. 7 is a partially sectional, top plan view depicting a socket and plug assembly at the trailing end of the novel housing.

The novel structure is completed by an electrical socket 70 (FIG. 7) that is formed in the distal end of wand body 12; it releasably receives an electrical jack or plug 72 that is connected to an elongate, unshielded conductor 74 having an adapter at its unillustrated opposite end for connection to a remote source of low voltage DC electrical power such as a remote automotive or motor home cigarette lighter plug, a battery pack, a wall adapter including a stepdown transformer and a rectifier, or the like.

Alternatively, an elongate unshielded power cord may be retractively received within the hollow interior of wand body 12, said power cord having a free end adapted for releasable connection to a remote source of power.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. An epilator, comprising:

a hollow wand body having an inner surface and an outer surface;

said wand body having a leading end and a trailing end;

an electrical circuit board for generating a predetermined radio frequency mounted within said trailing end of said wand body;

a metabolized conductive coating formed on said inner surface of said trailing end of said wand body to inhibit emission of electromagnetic radiation generated by said electrical circuit board, said inner surface of said leading end being free of said metabolized conductive coating;

a pair of opposed tweezer members mounted at said leading end of said wand body, said pair of opposed tweezer members including a first and a second tweezer member;

a bias means for maintaining said first and second tweezer members in a normally open configuration when said bias means is in repose;

an actuator member for compressing said bias means so that said first and second tweezer members are brought toward one another when said actuator member is manipulated;

an electrically conductive extension member that extends in a leading direction from said bias means and which is in electrical contact with said first tweezer member when said bias means is in repose;

an electrical contact member mounted in said second tweezer member;

said extension member making electrical contact with said electrical contact member when said tweezer members are brought toward one another;

said electrical contact between said extension member and said electrical contact member closing a circuit through said electrical circuit board when said first and second tweezer members are brought into said hair-gripping relation to one another so that a strand of hair gripped by said first and second tweezer members is subjected to said radio frequency, said radio frequency numbing nerve endings in the vicinity of said hair so that said hair may be painlessly uprooted;

whereby said electrical circuit board is contained within said hollow wand body and is shielded by said coating;

whereby said actuator combines a mechanical means for bringing said first and second tweezer members together and a switch means for activating and deactivating said electrical circuit board so that no separate on-off switch is required; and whereby a power cord leading from a remote power supply to said electrical circuit board need not be shielded.

2. The epilator of claim 1, further comprising:

electrically conductive means for interconnecting said electrical circuit board and said metabolized conductive coating.

3. The epilator of claim 2, wherein said electrically conductive means is provided in the form of a coil spring having a first end in electrically conductive communication with said electrical circuit board and a second end in abutting contact with said metabolized conductive coating.

4. The epilator of claim 1, wherein said wand body includes a first shell and a second shell, said first shell including a top wall and side walls depending from a periphery thereof, and wherein an actuator-receiving opening is formed in said top wall of said first shell;

whereby said actuator is manually manipulated when said wand is held in an operator's hand.

5. The epilator of claim 4, wherein said actuator includes a pair of transversely extending pivot pins that are pivotally supported within said hollow wand body.

6. The epilator of claim 4, wherein said first tweezer member includes a pair of transversely extending pivot pins that are pivotally supported within said hollow wand body.

7. The epilator of claim 1, wherein respective distal ends of said first and second tweezer members are cross-hatched and blunted so that said distal ends do not cut a strand of hair gripped between them and so that said distal ends make a substantially nonslipping gripping hold on a strand of hair gripped between them.

8. The epilator of claim 1, wherein said first and second tweezer members are plated with a nonoxidizable coating.

9. The epilator of claim 7, wherein said nonoxidizable coating is a gold plating having a thickness of about ten microns.

10. The epilator of claim 1, further comprising an electrical socket, formed in said hollow wand body, that is adapted to releasably receive an electrical plug that is connected to an elongate conductor having a preselected adaptor at a remote end thereof so that said electrical circuit board may be selectively connected to differing remote power sources.

11. The epilator of claim 1, further comprising an indicator light in electrical communication with said electrical circuit board so that said indicator light is activated when said circuit is completed through said electrical circuit board.

* * * * *